United States Patent [19]

Haberl et al.

[11] 4,128,335

[45] Dec. 5, 1978

[54] CONDENSATION NUCLEI COUNTER WITH AUTOMATIC RANGING

[75] Inventors: John B. Haberl; Janis Ozolins, both of Dalton, Mass.

[73] Assignee: General Electric Company, Schenectady, N.Y.

[21] Appl. No.: 772,230

[22] Filed: Feb. 25, 1977

[51] Int. Cl.$^2$ .............................................. G01N 1/00
[52] U.S. Cl. ...................................... 356/37; 356/341
[58] Field of Search .................................. 356/37, 103

[56] References Cited

U.S. PATENT DOCUMENTS

| | | | |
|---|---|---|---|
| 2,956,435 | 10/1960 | Rich | 356/37 |
| 3,010,308 | 11/1961 | Skala | 356/37 |
| 3,011,390 | 12/1961 | Van Luik, Jr. | 356/37 |
| 3,203,309 | 8/1965 | Skala et al. | 356/37 |
| 3,664,740 | 5/1972 | Rich | 356/37 |

Primary Examiner—John K. Corbin
Assistant Examiner—Matthew W. Koren
Attorney, Agent, or Firm—Joseph B. Forman; Francis K. Richwine

[57] ABSTRACT

A condensation nuclei counter for measurement of the concentrations of Aitken particles in gases by measurement of light scattered in a cloud chamber by water droplets formed on the particles in successive samples of a gas wherein the counter provides for sequential high speed sampling of the photodetector output during the cloud chamber growth of the droplets of each gas sample tested as a way of measuring the rate of increase of total droplet cross-section and wherein the counter provides for automatic ranging for particle population coordinated with the timed sampling during particle growth.

12 Claims, 4 Drawing Figures

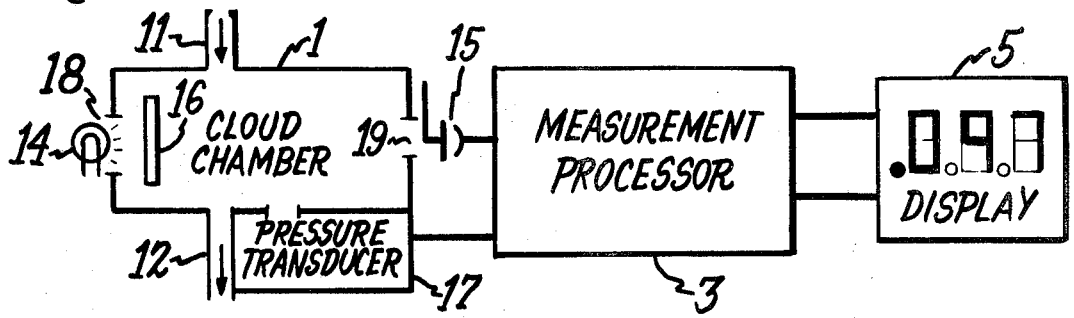
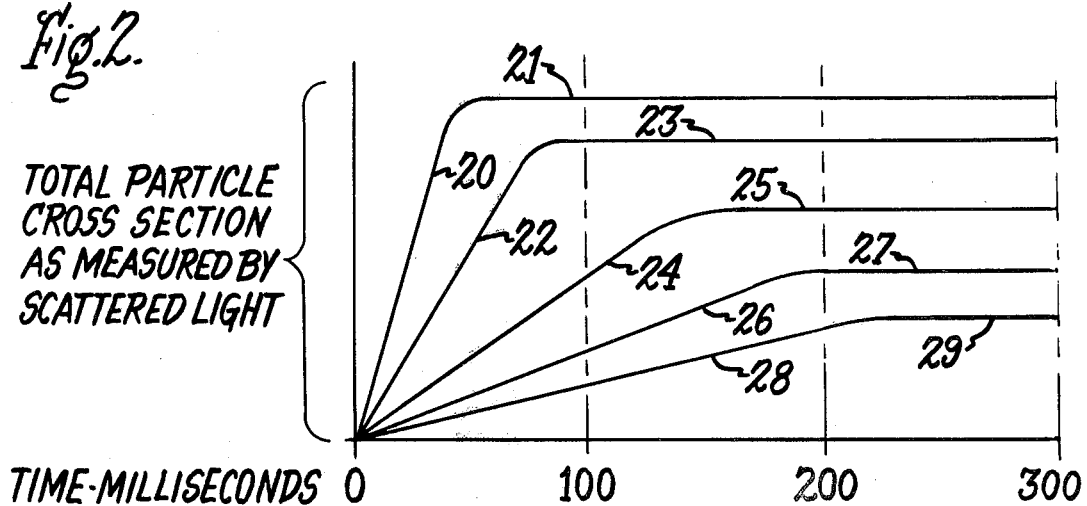
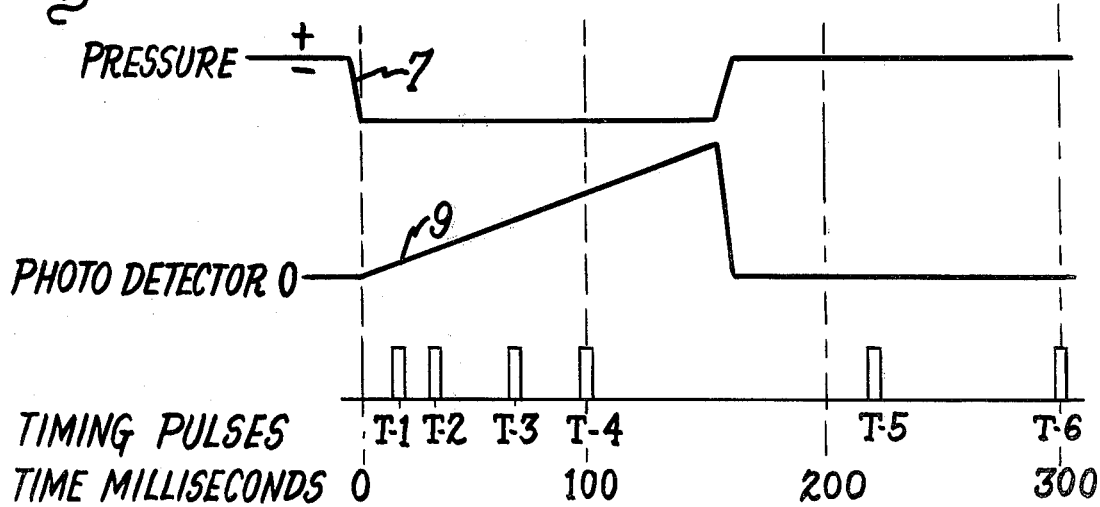

CONDENSATION NUCLEI COUNTER WITH AUTOMATIC RANGING

BACKGROUND OF THE INVENTION

1. Field of the Invention

It is common to measure Aitken nuclei (airborne particles in the approximate size range of $10^{-7}$ to $10^{-5}$ centimeters radius) by the condensation of water vapor on the particles in a cloud chamber to produce optically detectable droplets of several micrometers in diameter (1 to $10 \times 10^{-4}$ cm) which are either photographed for counting or measured photometrically by measuring the intensity of scattered light or the attenuation of light passed in a fixed volume. A standard technique used in Aitken nuclei counters is to humidify the sample of gas to be tested to approximately the saturation point and subject the sample to an adiabatic expansion to lower the temperature to well below the dew point causing the excess water vapor of the super-saturated sample to condense upon any particles present. It has been established through experimentation that droplet growth cross-sectionally (radius squared) is essentially linear with time as long as excess water vapor from the super-saturated condition is available. Growth stops when the super-saturated condition ceases to exist. In photometric measurement by measurement of the scattering of light, it is common to use a dark field optical system, illuminating the cloud chamber with light and using a photodetector to view the light scattered by the droplet formed. The light source, the photodetector and baffles are placed in the chamber in such a way that the photodetector sees no light directly from the source and thereby measures only the intensity of scattered light.

2. Description of the Prior Art

The prior art is well represented by the device of Skala and Rich as described in U.S. Pat. No. 3,203,309, issued Aug. 31, 1965, which is made up of a cloud chamber adapted for the repetitious purging, charging with gas samples, adiabatic expansion and the measurement of light scattered by droplet growth about the Aitken nuclei and particle measurement means, as for example electronic circuitry, which converts the intensity of the scattered light to an electrical output signal at some predetermined stage of the particle growth for each gas sampling. Generally, the prior art read-out circuitry produces a reading on an instrument, such as a voltmeter, of a peak value obtained or of a reading at a particular time. They may also include means for comparison of readings with a reference standard and they may include other features such as means providing for step functions as disclosed in Skala and Rich. It appears that the art as represented by Skala and Rich and also by Skala, U.S. Pat. No. 3,010,308; VanLuik, U.S. Pat. No. 3,011,390, Rich, U.S. Pat. No. 2,956,435; and others displays a need for a more sophisticated measurement system which will provide for wide range linearity without sacrificing sensitivity.

SUMMARY OF THE INVENTION

The invention contemplates a condensation nuclei counter in which there is an improvement in measurement as a result of the plurality of measurements made during droplet growth in each sample tested and of the automatic ranging technique which obviates the need for conscious selection of density ranges. These features combine to assure a more linear response. This is accomplished by providing for a plurality of measurements of scattered light during the period that droplet growth would be possible, discarding all measurements in excess of an arbitrarily assigned value, and using a predetermined multiplier for a final readout the value of which depends upon which of the sequential measurements is the one used.

DESCRIPTION OF THE DRAWINGS

FIG. 1 is a functional block diagram of a condensation nuclei counter according to the invention;

FIG. 2 is a graphic depiction of a wide range of droplet growths which can be encountered by a condensation nuclei counter;

FIG. 4 is a graphic representation of the occurrences of the timing pulses in relationship to the cycle of the adiabatic expansion of sample tested and the resultant particle growth.

DESCRIPTION OF THE INVENTION

Figure 3:
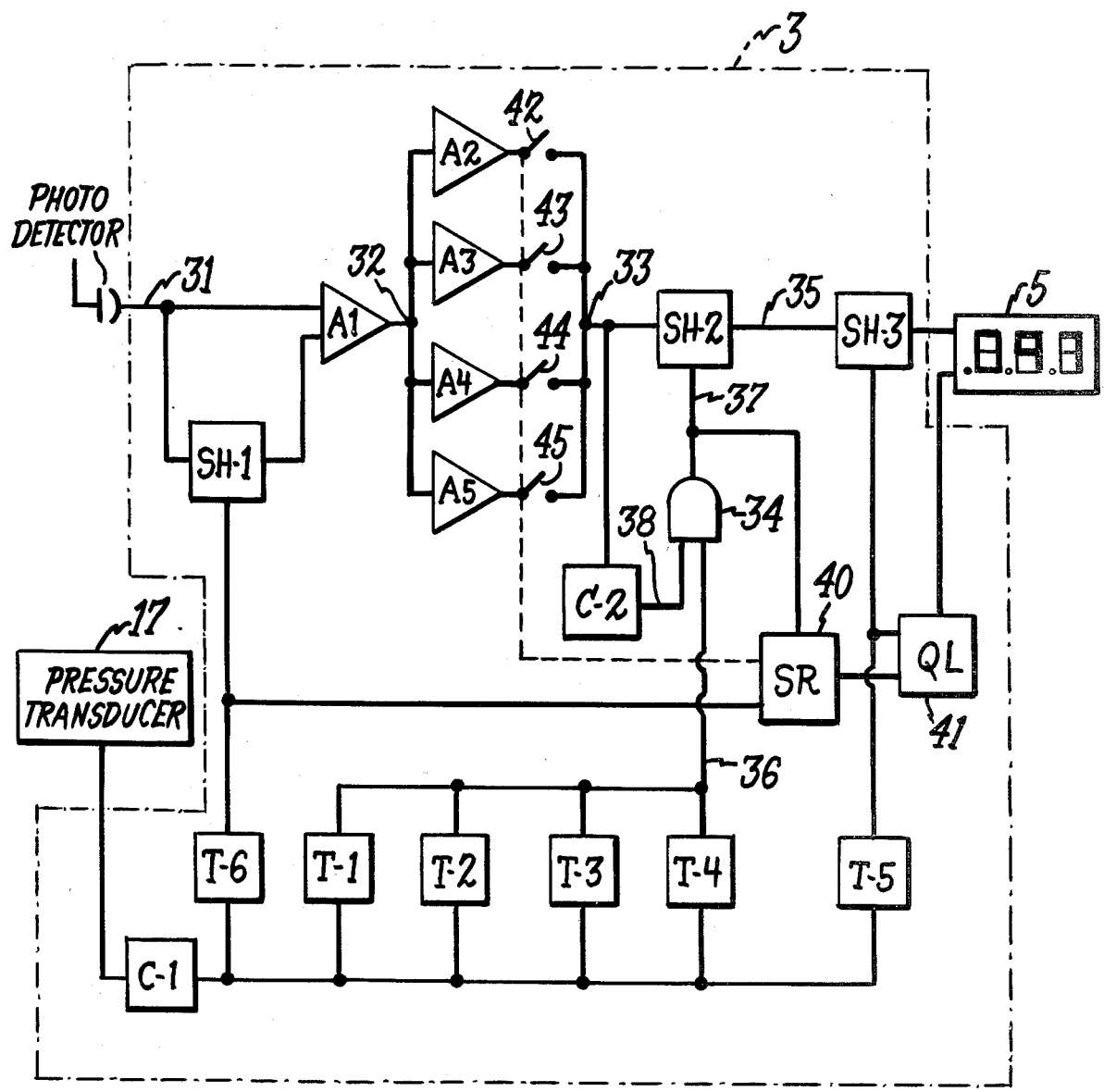
FIG. 3 is a functional block diagram of a portion of a condensation nuclei counter according to this invention more fully showing the improvements according to this invention.

FIG. 1 shows in block diagram the principal components of a condensation nuclei counter device of a type to which this improvement applies. As shown, this device includes a cloud chamber 1, a measurement processor 3, and a display device 5, wherein cloud chamber 1, which may be as disclosed by Skala in U.S. Pat. Nos. 3,010,308 or 3,203,309 or similar devices, includes as essential elements a gas handling system, represented symbolically by conduits 11 and 12, for charging the chamber with a humidified gaseous sample, for causing partial evacuation of the sample to provide an adiabatic expansion and for purging the chamber prior to acceptance of a new sample; an illuminating device 14; a photoelectric device 15; and baffle means 16 to prevent the photoelectric device 15 from being directly illuminated by the light source 14. This improvement in condensation nuclei counters also requires a coordinating means which in our preferred embodiment is a pressure transducer 17 attached to the cloud chamber to generate a signal which is a measurement of the pressure in the cloud chamber, although alternatives such as Skala and Rich's cams 44, 55 or valve driven means could be used to indicate the fact of the sample expansion. As summarized above with respect to the background of the invention, each successive sample of a gas in which the population of Aitken particles is to be determined is placed in the cloud chamber 1 in a humidified condition and reduced in pressure by the evacuation of a portion of the sample resulting in an excess humidity that causes formation of water droplets about the Aitken nuclei. The gas handling system including necessary vacuum pumps, valves, humidifier and controls for operation of the cloud chamber are not shown as there are several acceptable ways of accomplishing this within the state of the art. Light from light source 14 entering the chamber through a window 18 will be scattered by the droplets as they grow in the cloud chamber and can be observed by the photoelectric device 15 through the window 19. Baffle devices, as represented by 16, block the direct light path between windows 18 and 19. A signal generated by the photoelectric device 15 is used to generate a relevant particle population count.

It is well known that cross-section growth of each droplet is essentially linear with time as long as sufficient excess water vapor is available during the period that the sample stays below the dew point in pressure and temperature. Total droplet cross-sectional growth is, therefore, linearly proportional to particle population and the scattering of light by the droplets is directly proportional to the total cross-sectional area of all of the droplets. Thus, it can be appreciated that the rate of growth of the total cross-sectional area is a measurement of particle density. This invention is directed toward use of that concept as a basis for measurement.

FIG. 2 shows a selection of total particle cross-section growth according to time for several hypothetical samples. Plots 20 and 28 are intended to illustrate extreme samples, i.e., plot 20 corresponds to a sample which has a high population of Aitken particles and 28 indicates a sample which has a very low population. In the case of the high population as indicated by plot 20, there is a very fast total particle cross-section growth because of the high number of particles which exhausts the excess humidity in a very short time to cause the total particle cross-section to level off early in elapsed time to a constant figure as represented by portion 21 of the plot. The situation with the sample depicted by plot 28 differs only in that the fewer particles, although each is growing at the same rate as those of plot 20, take a much longer period of time to exhaust the excess humidity before cessation of total cross-section growth as indicated by the later levelling out at 29 of plot 28. Intermediate plots 22, 24 and 26 serve to illustrate intermediate concentrations. The slope of each plot portion 20, 22, 24, 26 and 28 is a measurement of the particle concentration.

One measurement problem solved by this invention is created by the fact that there is no single time at which all of the samples represented by the plots 20-28 can be reliably measured as measurements to be accurate must be made at a time during particle growth at which there is sufficient total cross-sectional area to be measured by light scattering and prior to exhaustion of the excess humidity. For example, although measurements at 8 and 15 milliseconds on the scale indicated would show a measurable cross-sectional area for plot 20, they would be of impractically low values for plot 28. Conversely, measurements made at much later times, for instance at 50 or 100 milliseconds, while being appropriate for plots 26, 28 would not yield linear response responses for plots 20, 22. The solution, therefore, and one to which this invention is directed, is to make a plurality of measurements within the scope of possibilities, using as a result the measurement which is appropriate for the concentration of particles encountered. (This may be referred to as ranging, or dividing the entire scope into ranges.) On a theoretical basis, this is to say that the concentrations represented by plots 20-22 could best be measured somewhere within the times of 10-30 milliseconds and concentrations represented by plots 26-28 could best be measured in the times of growth between 80 and 150 milliseconds. The preferred embodiment of the present invention contemplates the measurement of growth at a plurality of times after the adiabatic expansion takes place and then, by processing the readings taken, selecting the most appropriate reading for growth rate and using it to generate the counter's output.

This desired result, i.e., making a plurality of readings and selecting and processing for final output the one most appropriate to the concentration encountered, is accomplished by our improvement in signal processing as represented schematically in FIG. 3 as a particular embodiment of the portion 3 of the condensation nuclei counter illustrated in FIG. 1. Two inputs are received by processor 3 of which one is the signal received from the photodetector 15 which is (in the device as reduced to practice and marketed as the General Electric Condensation Nuclei Counter CNC-2) an analog measurement of the intensity of the scattered light and, therefore, a linear measurement of the total particle cross-section at any particular time of the droplets formed on Aitken particles as a result of the adiabatic expansion of the humidified sample. The other input is from the transducer 17 and is a signal representing the pressure in the cloud chamber. These two signals are represented graphically by plots 7 and 9 of FIG. 4. Signal 7 representing the pressure in the cloud chamber is a control signal and signal 9 which is a measurement of the intensity of scattered light in the cloud chamber at any particular time is the substantive signal on which the condensation nuclei counter output will be based. The coordinating signal 7 is received by comparator C1 (FIG. 3) and, on the occasion of a drop in the pressure in the cloud chamber resulting from the partial evacuation of the chamber to cause the adiabatic expansion to below a preset level, causes comparator C1 to initiate timing sequences by a signal transmitted to a clock structure in the form of timing circuits T1 through T6. Each of the timing circuits generates an output pulse at a predetermined time after the T=0 pulse signal transmitted by comparator C1. Each of the six time periods is different and the use of each one will be described more fully below.

The photodetector output signal 9 is transmitted simultaneously to sample and hold circuit SH1 and amplifier A1. These two components SH1 and A1 form a dc restorer circuit to compensate for the fact that the output of the photodetector contains both an ac and a dc component. The ac component contains the desired information on the amount of scattered light caused by the particle growth and the dc component results from stray light in the system and photodetector baseline drift. The dc component is removed by sampling and holding it in SH1 from a time before the adiabatic expansion of the sample in the cloud chamber and reversing the polarity of the dc voltage and combining it in amplifier A1 with the instantaneous total signal received directly from the photodetector. This causes amplifier A1 to produce at 32 a signal that is an amplification of the ac portion of the signal at 31 and which is a function of the light in the cloud chamber as scattered by the Aitken particles as measured by the photodetector. The amplified signal at 32 is then further amplified by one of the four amplifiers A2 through A5 and made available at 33 for further use. The four amplifiers A2-A5 are switched in and out of operation selectively by shift register 40 operating switches 42-45 so that only one of the amplifiers is in operation to amplify the signal at 32 at any one time. The amplified signal at 33 is applied to the input of sample and hold circuit SH2 which on command of gate 34 provides a signal of the input of SH2 at the time of the command on line 35 to the input of sample and hold circuit SH3 where it is available for ultimate transfer to display 5. Each signal placed into SH2 being a measurement of droplet size at a particular time is, of course, a measurement of rate of growth up to the command time.

Actions of the amplifiers A2-A5 and sample and hold circuits SH2 and SH3 and the ultimate display of a value on the display 5 are controlled through the timing circuits T1 through T6. Comparator C1, as noted above, monitors the output signal of pressure transducer 17 and generates an initiating pulse for timers T1 through T6 at the time that the pressure transducer indicates a pressure drop which is a measurement of the commencement of adiabatic expansion of the gas sample. Each of the six timers generates an output pulse at a specifically selected time subsequent to the zero time initiating pulse received from comparator C1. Each of the timers T1 through T4 has its predetermined time selected empirically as will be explained below in connection with the operation of and values of the amplifiers A2 through A5. The timing cicuits T1 through T4 which are sample selectors each generates a pulse at its prescribed time and transmits that pulse on line 36 to gate 34. Gate 34, unless blocked by a signal generated by comparator C2, as will be explained later, passes the timing pulse on line 37 to both sample and hold cicuit SH2 and to the shift register 40. On each timing pulse through gate 34, SH2 will accept and hold and transmit on line 35 the value then existing at 33 and, as a result of the same pulse from the gate, the shift register 40 will advance the engaged one of the four amplifiers A2 through A5 to the next higher numbered amplifier by connecting/disconnecting switches 42-45 in sequence. In addition, the shift register 40 advances the decimal value input to quad latch 41 to the next order of magnitude.

Timing circuit T5 is programmed to produce its output pulse after completion of the sample measuring sequence to produce an output reading by commanding shift register SH3 and quad latch 41 to convey their retained values to display 5. Display 5 as illustrated is a digital display device which will show three significant figures and four possible locations of a decimal point with the three significant figures being controlled by the value held at the command time by sample and hold circuit SH3 and the decimals will be located according to values stored in the quad latch 41. Timing circuit T6 generates its pulse subsequent to that of T5 and in effect terminates the cycle and readies the circuit for the following cycle by commanding sample and hold circuit SH1 to take a new reading on the "at rest" conditions and by commanding shift register 40 to assume its prestart condition with switch 42 closed and switches 43, 44 and 45 open.

The display device 5 as illustrated and explained is a commercially obtainable display device and is not limiting upon our invention since other equally effective display or recording systems are available which could be used with our invention.

The substance which causes this improvement to constitute invention resides in our preferred embodiment in the arrangement and coordination of the four amplifiers A2 through A5, the four timing circuits T1 through T4, comparator C2 and gate 34. As previously noted, the object of the invention is to measure the growth rate of the total cross-section of the particles as a measurement of particle population, to make those measurements sequentially on different scales during growth and to use the measurement that is most appropriate to the concentration found, i.e., a measurement after sufficient growth and prior to exhaustion of excess humidity. The latter feature can be referred to as automatic ranging.

It was also noted that a high population requires early measurement whereas a low population density is best measured at a later time. FIG. 4 shows selected timing pulses representing four specific sampling times selected empirically, each of which could give a reasonable result for some range of densities. The object is to have the four timing pulses for taking readings to cover linearity to high concentrations as previously discussed with respect to the plots in FIG. 2. Although on a theoretical basis, it would appear to be convenient to increase each time period by a factor of 10 over the previous one, that is not completely practical. One set of times that has been shown empirically to be practical has been 8, 15, 50 and 100 milliseconds after the adiabatic expansion. These are values similar to those indicated on FIG. 4. With the combination of shift register 40 and the bank of four amplifiers A2 through A5 set with switch 42 closed at the commencement of the cycle, each amplifier A2 through A5 is associated with a particular timing pulse, the timing pulse generated by T1 causes a reading to be taken through switch 42 and amplifier A2 and causes the shift register 40 to open switch 42 and close switch 43 so that the pulse generated by T2 causes a reading to be made from the output of amplifier A3. Subsequent pulses advance the switching system first to amplifier A4 and secondly to A5 to provide automatic ranging. Each of the amplifiers A2 through A5 provides for a different amplification of the signal existing at 32 so that there is an increased sensitivity to provide for a situation in which the concentration might correspond to a low population as indicated by either plot 26 or 28 in FIG. 2. By comparing FIGS. 2 and 4, it can be seen that the measurements made at T1 and T2 would be most appropriate for concentrations or population ranges comparable to those indicated by plots 20 and 22 in FIG. 2 and that pulses T3 and T4 would be more appropriate for concentrations in the range of those indicated by plots 24, 26 and 28. Therefore, the values of amplifiers A2 through A5 are selected so that each higher number has an amplification higher than the preceding one yielding an overall difference in signal amplitude on line 33 by a factor of 10 between successive measurement commands. This automatic ranging is completed by the use of comparator C2 and gate 34 interdicting the timing pulses on line 26 enroute to sample and hold circuit SH2. Comparator C2 compares the amplifier output signal at 33 with a predetermined value which is selected as a maximum reading based on a total cross-section of droplets that is known, or can be calculated, as being safely below the total droplet cross-section that would occur at the exhaustion of the excess humidity at which time droplet growth would cease. This precludes the taking of measurements beyond the time that the total cross-section growth of droplets remains linear or with particle population or concentration. At any such time as this maximum value is exceeded, comparator C2 places a signal on line 38 which causes gate 34 to block further timing pulse signals on line 36. This means, for example, that should a sampling signal such as the pulse from timer T2 cause an advancement of amplifiers to A4 by the opening of switch 43 and the closing of switch 44 after the sample and hold circuit SH2 has accepted the value produced by amplifier A3 and comparator C2 finds that the signal now at 33 being produced by amplifier A4 exceeds the predetermined maximum value, then, by means of a signal on line 38, the gate 34 is switched off blocking the subsequent timing pulses produced by timing circuits T3 and T4. In this case, sample and hold circuit SH2 and the shift register 40 would continue to hold the values which correspond to that already accepted from amplifier A3 on the occurrence of the timing pulse generated by T2 until sample and hold circuit SH3 and the quad latch 41 are commanded by T5 to convey that concentration measurement to the display unit. As noted above, an amplification factor of 10 is a designed objective in the bank of the four amplifiers and selected as far as possible to correspond to full scale measurement values of $10^6$, $10^5$, $10^4$ and $10^3$ nuclei per cubic centimeter. Certain modifications, of course, must be made since time periods less than several milliseconds do not yield droplets of adequate size in any case and time periods in excess of several hundred milliseconds will allow heat flow from the chamber walls to interfere with growth process. A certain amount of selection based on experience is required to establish the best practical correlation between the amplification ratios of the bank of four amplifiers and the times of pulses generated by the four timing circuits within the foregoing teaching.

It must also be appreciated that since the basic concept of this invention is the use of the rate of growth of total droplet cross-section as a measurement, that other implementations of the basic concept are at least theoretically possible. However, we believe that our preferred embodiment disclosed is the most practical implementation and, therefore, the best mode of carrying out the invention. Measurement might, for example, be accomplished by measuring the length of time for total droplet cross-section to reach a predetermined value and drive a counter by this time measurement.

From the foregoing detailed explanation, it can be appreciated that a condensation nuclei counter according to our improvement provides for the taking of sequential measurements of total cross-section during growth of water droplets about Aitken nuclei following adiabatic expansion of the sample and that by using a predetermined magnitude of amplification of the measurement signals the several measurements can then be screened automatically to select the last one of the multiple readings which does not exceed a predetermined maximum total cross-section measurement to use as the final measurement. By having these multiple measurements and screening accomplished during every sample of the gas to be examined, it is possible to have a condensation nuclei counter which when calibrated and adjusted against standards will be ready for use to automatically measure and record a wide range of possible concentrations. This is a useful improvement as many condensation nuclei counters are used in circumstances in which it is not practical to have an operator make the required adjustments to the machines to accomodate varying conditions. The counters of Skala and Rich and others of the prior art must be preset to be ready to measure concentrations within estimated ranges. Since our improved machine is useable with recording devices or remote transmission systems as well as a locally readable display such as the one illustrated and described, an improved condensation nuclei counter according to our invention constitutes a substantial advancement in the art.

We claim:

1. In a condensation nuclei counter including cloud chamber means for condensing liquid droplets about Aitken particles to be measured in successive rate of growth samples represented by rate of growth signals, dark field means for illuminating the cloud chamber, photo sensitive means for producing a photoelectric signal proportional to light scattered by said droplets and from which said rate of growth signals are developed, pressure transducer means for sensing the pressure in said chamber dropping below a predetermined level, and quantitating means for producing an output signal indicating the Aitken particle concentration of the sample, the improvement wherein said quantitating means comprises:
    (a) means for applying said rate of growth signals to the inputs of a plurality of amplifiers each of said amplifiers having an output and each amplifier being of a different predetermined gain;
    (b) means for storing signals representative of predetermined maximum values selected for a total cross-section of droplets that are known;
    (c) means for successively comparing the output signal of said amplifiers in ascending order of their gain against the stored signals representative of the maximum values selected for a total cross-section of droplets that are known in their descending order of value;
    (d) means for selecting the first photoelectric amplified signal that exceeds the first stored maximum value signal during said sequential comparing; and
    (e) output signal means responsive to said selected signal for producing said output signal.

2. The improved condensation nuclei counter of claim 1 wherein said comparing means comprises:
    (a) clock means for producing a plurality of signals at predetermined times; and
    (b) means for producing said plurality of sequential rate of growth signals and comparing said signals to said stored signals representative of the predetermined maximum value signals responsive to said time signals.

3. The improved condensation nuclei counter of claim 2 wherein said amplifier means comprises:
    (a) multiple amplifiers each being responsive to a different one of said time signals to produce one of said sequential signals.

4. The improved condensation nuclei counter of claim 2 wherein said quantitating means further comprises:
    (a) storage means responsive to said clock means and to said amplifiers for accepting and storing said amplified signals as said sequential signals on command of time signals;
    (b) sequencing means responsive to said clock means for sequentially accessing said storage means to each of said amplifier means; and
    (c) comparator means for comparing said amplified signals with a predetermined threshold value exemplified by said stored maximum values and for selecting as said measurement signal a sequential signal stored in said storage means when one of said amplified signals reaches said threshold.

5. The improved condensation nuclei counter of claim 1 wherein said quantitating means further comprises:
    (a) clock means responsive to the time of beginning of condensation for producing time signals measuring time from said time of beginning,
    (b) amplifier means for producing amplifications of said photoelectric signal; and
    (c) storage means responsive to said clock means and to said amplifier means for receiving and storing said amplifications at the time of said time signals to constitute said sequential signals,
    (d) sequencing and comparator means responsive to said amplifier means, to said clock means and to a threshold value indicative of completion of condensation for selecting as said measurement signal the last sequential signal prior to an amplification crossing said threshold whereby said sequential signal selected constitutes the highest rate of total droplet cross-section growth measured during the period of adequate excess humidity in the sample to permit linearity between rate of growth and particle concentration.

6. A condensation nuclei counter for measurement of concentrations of Aitken particles in gases comprises:
(a) a cloud chamber having means for repetitively charging and purging the chamber with humidified gas samples, means for adiabatically expanding said samples while the chamber, dark field illumination means, photosensitive means for observing and for generating a photoelectric signal proportional to light scattered by liquid droplets condensing on Aitken particles in said chamber and coordinating means for producing a zero time signal indicating the time of occurrence of the adiabatic expansion which starts droplet formation;
(b) quantitating means including clock means responsive to said zero time signal for producing a plurality of time signals for measuring time of droplet growth, amplifier means responsive to said photoelectric signal for producing amplifications of said photoelectric signal representing the extent of droplet growth, sampling means responsive to said amplifications and to said time signals for producing a plurality of measurements of rate of droplet growth, means for selecting one of said plurality of measurements as the measurement signal according to an established criteria, output signal means responsive to said selected measurement signal for producing a quantitating means output signal; and
(c) data processing means for converting said output signal to human readable form.

7. The condensation nuclei counter of claim 6 wherein said amplifier means is compound so as to simultaneously produce plural magnitudes of amplifications which may be selected.

8. The condensation nuclei counter of claim 7 wherein:
(a) said sampling means includes means for storing said sequential measurements,
(b) said means for selecting includes means for comparing said amplifications with a predetermined threshold, and
(c) said means for selecting includes means responsive to said comparator means for selecting a stored sequential measurement when one said amplification exceeds said threshold.

9. The condensation nuclei counter of claim 6 wherein said plurality of time signals measuring time of droplet growth are sequential signals produced at predetermined times of growth whereby each said time signal in combination with the output of said amplifier at such time produces a measurement of droplet growth during the period from zero time to said time signal.

10. The condensation nuclei counter of claim 9 wherein said amplifier means is compound so as to simultaneously produce plural magnitudes of amplifications.

11. The condensation nuclei counter of claim 10 wherein:
(a) said sampling means includes means for storing said sequential measurements,
(b) said means for selecting includes means for comparing said amplifications with a predetermined threshold, and
(c) said means for selecting includes means responsive to said comparator means for selecting a stored sequential measurement when one said amplification exceeds said threshold.

12. The condensation nuclei counter of claim 10 wherein each magnitude of amplification and time signal set to which said sampling means is responsive is a mutually exclusive set whereby said means for selecting performs automatic ranging.

* * * * *